(12) United States Patent
Tanaka et al.

(10) Patent No.: US 8,486,433 B2
(45) Date of Patent: Jul. 16, 2013

(54) ANTIBACTERIAL DEODORANT

(75) Inventors: Atsushi Tanaka, Kitakyushu (JP);
Tsuguo Koyanagi, Kitakyushu (JP)

(73) Assignee: JGC Catalysts and Chemicals Ltd.,
Kawasaki-Shi (JP)

( * ) Notice: Subject to any disclaimer, the term of this patent is extended or adjusted under 35 U.S.C. 154(b) by 1540 days.

(21) Appl. No.: 11/117,329

(22) Filed: Apr. 29, 2005

(65) Prior Publication Data

US 2006/0286051 A1    Dec. 21, 2006

(30) Foreign Application Priority Data

May 7, 2004   (JP) ................................ 2004-138472
Sep. 21, 2004  (JP) ................................ 2004-272776

(51) Int. Cl.
*A61K 8/28*   (2006.01)
*A61K 8/58*   (2006.01)
*A01N 25/28*  (2006.01)

(52) U.S. Cl.
USPC ............................ 424/421; 424/66; 424/405

(58) Field of Classification Search
USPC ....................................................... 424/401
See application file for complete search history.

(56) References Cited

U.S. PATENT DOCUMENTS

| 4,906,466 | A | * | 3/1990 | Edwards et al. | ............... | 424/421 |
| 5,413,788 | A | * | 5/1995 | Edwards et al. | ............... | 424/409 |
| 5,723,110 | A | * | 3/1998 | Yamamoto et al. | ............. | 424/65 |
| 2002/0005145 | A1 | * | 1/2002 | Sherman | ....................... | 106/436 |

FOREIGN PATENT DOCUMENTS

| EP | 0937398 A1 | * 8/1999 |
| JP | 01-258792 | 10/1989 |
| JP | 02-225402 | 9/1990 |
| JP | 03-275627 | 12/1991 |
| JP | 04-321628 | 11/1992 |
| JP | 06-080527 | 3/1994 |
| JP | 07-033616 | 2/1995 |
| JP | 10-017406 | 1/1998 |
| JP | 2004-091263 | 3/2004 |

OTHER PUBLICATIONS

Chen, Y., Preparing titanium oxide with various morphologies, Elsevier, Materials Chemistry and Physics 81 (2003) 39-44.*

* cited by examiner

*Primary Examiner* — Carlos Azpuru
(74) *Attorney, Agent, or Firm* — Manabu Kanesaka

(57) ABSTRACT

Present invention provides an antibacterial deodorant with antibacterial characteristics and high deodorizing capability. The antibacterial deodorant is inorganic oxide particles comprising a metal component and an inorganic oxide other than the metal component, the inorganic oxide includes titanium oxide and silica and/or zirconia, and the titanium oxide is crystalline titanium oxide. A content of the metal component in the inorganic oxide particles is in a range from 0.1 to 30% by weight as converted to an oxide thereof, and an average particle diameter of the inorganic oxide particle is in a range from 2 to 500 nm.

11 Claims, No Drawings

ANTIBACTERIAL DEODORANT

The present application refers to Japanese Patent Application Number 2004-138472 filed on May 7, 2004 and Japanese Patent Application Number 2004-272776 filed on Sep. 21, 2004.

BACKGROUND OF THE INVENTION AND RELATED ART STATEMENT

The present invention relates to an antibacterial deodorant, and more particularly to an antibacterial deodorant which shows the antibacterial effect, deodorizing effect, and mildewproof capability when added in or applied to resins, paints, textiles, paper, unwoven cloths, leather, furniture, cosmetics, glass, tile, concrete, and the like.

There have been known antibacterial compositions comprising a metal component having the antibacterial characteristics carried on powder of such materials as zeolite, silica gel, or titanium oxide, and the antibacterial compositions are disclosed, for instance, in Japanese Patent Laid-Open Publication No. HEI 2-225402 (Patent document 1).

However, the known powder antibacterial compositions have the problems as described below:
(1) the dispersibility is low when added in resins, paints, textiles, leather, cosmetics, and the like;
(2) the antibacterial capability is not expressed effectively, and it is necessary to add the antibacterial composition by a large volume for obtaining the desired antibacterial activity;
(3) the powder easily aggregates when the added volume increases, and further as a content of the metal component increases, the color change may occur in the composition using an antibacterial metal component such as silver;
(4) when the antibacterial composition is added in a resin as a raw material for fiber spinning, thread breakage easily occurs when the thread is produced with composition powder with a large diameter;
(5) when a paint containing the antibacterial composition in the powder state is applied on a surface of a material such as a resin for forming a coating film with the antibacterial capability, the film thickness is large and the film strength is rather low, and in addition film peeling easily occurs. Further the composition can not be used when the transparency is required;
(6) the film peeling easily occurs also when a paint containing the antibacterial composition in the powder state is applied to a surface of leather or the like, and the texture and color may sometimes be undesirable.

The present inventors proposed, in Japanese Patent Laid-Open Publication No. HEI 3-275627 (Patent document 2), a novel antibacterial composition prepared by exchanging metal ions in a salt of inorganic oxo acid with ions of metal having the antibacterial characteristics, but the composition cannot always satisfy the requirements for solving the problems described above.

Japanese Patent Laid-Open Publication No. HEI 1-258792 (Patent document 3) proposes an antibacterial agent containing alumina sol having the antibacterial characteristics with a metal having an antibacterial function or a compound thereof deposited on a surface of aluminum oxide in the alumina sol. It can be guessed that the invention dissolves the problem (5) making use of a coating film forming-function possessed by alumina sol, but the problems (1) to (4) are still kept unsolved.

Further Japanese Patent Laid-Open Publication No. HEI 4-321628 (Patent document 4) proposes an antibacterial agent comprising silver colloidal particles having the high antibacterial performance, but the colloidal solution has a grey color and lacks the transparency. In addition, the silver component itself is colloidal particles, and therefore there is the problem that the antibacterial agent easily aggregates and lacks the stability.

To solve the problems specific to the antibacterial composition or deodorizing compositions in the power state as described above, the present inventors proposed, in Japanese patent Laid-Open Publication No. HEI 6-80257 (Patent document 5) and Japanese Patent Laid-Open Publication No. HEI 7-33616 (Patent document 6), an antibacterial agent comprising a novel colloidal solution of antibacterial inorganic oxide.

Japanese Patent Laid-Open Publication No. HEI 7-33616 (Patent document 6) proposes an antibacterial inorganic oxide colloidal solution in which particles comprising an antibacterial metal component and an inorganic oxide other than the antibacterial metal component are dispersed, and the antibacterial inorganic oxide colloidal solution is characterized in that, assuming A indicating a weight of the antibacterial metal component in the colloidal solution and B indicating a weight of the antibacterial metal component segregated by subjecting the colloidal solution to the ultra-centrifugal processing, a value for an index of coupling expressed by B/A is $1.0 \times 10^{-3}$ or below, and discloses a method of preparing the antibacterial agent by heating an aqueous solution of titanium oxide obtained by adding hydrogen peroxide in a gel or a sol of hydrated titanic acid and an aqueous solution of an antibacterial metal component in the presence of a silicon compound and/or a zirconium compound.

The problems (1) to (6) have been solved by the inventions above to some extent, but sometimes the odor eliminating performance is insufficient, thus, in some applications, an antibacterial deodorant having the further sufficient odor eliminating performance is needed. Especially, the so-called sick house syndrome is seen as a social problem in relation to the living environment or residential environment, and deodorants are required to have the capability of killing ticks, fleas, and the like, the capability of decomposing odorous organic compounds such as aldehyde, toluene, xylene, and further the capability of eliminating harmful gasses such as carbon monoxide and organic materials such as tar generated in association with smoking.

To clean the living environment as described above, there has been proposed a method of producing various types of antibacterial agents and deodorants each including titanium oxide having the photocatalytic effect.

For instance, Japanese Patent Laid-Open Publication No. 2004-91263 (Patent document 7) proposes a method of producing a anatase-type titania sol comprising the steps of mixing an aqueous solvent solution of a titan compound expressed by the formula of $TiX_4$ (X indicates an halide ion or an alkoxy group) to generate titanium hydroxide; mixing the titanium hydroxide with an acid; and heating the mixture to a temperature in the range from 20 to 90° C., and this document includes descriptions concerning the fact that the anatase-type titania has the photocatalytic characteristics such as the antibacterial activity, decontaminating capability, and odor eliminating characteristics. However, because the anatase-type titania sol does not include any antibacterial and odor-eliminating metal component, the antibacterial activity and odor-eliminating effect are disadvantageously small.

The present inventors proposes in Japanese Patent Laid-Open Publication No. HEI 10-17406 (Patent document 8) an antibacterial agent comprising a colloidal solution with fiber-like inorganic oxide particles including titanium oxide dispersed therein as an antibacterial agent having the excellent durability against, for instance, washing. However, the titanium oxide included in this antibacterial agent is amorphous titanium oxide, and as the fiber-like particles are dispersed in the colloidal solution, when this antibacterial agent is used for textile, the fiber-like colloidal particles show a strong adhesive force without using any binder.

[Patent document 1] Japanese Patent Laid-Open Publication No. HEI 2-225402
[Patent document 2] Japanese Patent Laid-Open Publication No. HEI 3-275627
[Patent document 3] Japanese Patent Laid-Open Publication No. HEI 1-258792
[Patent document 4] Japanese Patent Laid-Open Publication No. HEI 4-321628
[Patent document 5] Japanese Patent Laid-Open Publication No. HEI 6-80527
[Patent document 6] Japanese Patent Laid-Open Publication No. HEI 7-33616
[Patent document 7] Japanese Patent Laid-Open Publication No. 2004-91263
[Patent document 8] Japanese Patent Laid-Open Publication No. HEI 10-17406

SUMMARY OF THE INVENTION

The present inventors made strenuous efforts for solving the problems described above, and found that, in an inorganic oxide used for preparing an antibacterial agent and comprising titanium oxide and silica and/or zirconia, especially when the titanium oxide is crystalline titanium oxide, and specifically anatase-type titanium oxide, the inorganic oxide shows not only the antibacterial activity, but also excellent photocatalytic activity and odor-eliminating effect. The present invention is based on this discovery.

Namely, an object of the present invention is to provide, for solving the problems (1) to (6) above, an antibacterial deodorant having both the antibacterial activity and high odor-eliminating activity and a method of producing the same.

The antibacterial deodorant according to the present invention is inorganic oxide particles comprising a metal component and an inorganic oxide other than the metal component, and is characterized in that the inorganic oxide comprises titanium oxide and silica and/or zirconia, and the titanium oxide is crystalline titanium oxide.

The titanium oxide is anatase-type titanium oxide and a crystallite diameter of the titanium oxide is preferably 100 Å or more.

A content of the metal component in the inorganic oxide particles is preferably in the range from 0.1 to 30% by weight as converted to the metal oxide.

The average particle diameter of the inorganic oxide particles is preferably in the range from 2 to 500 nm.

The antibacterial deodorant according to the present invention is a dispersion liquid of inorganic oxide particles comprising a metal component and an inorganic oxide other than the metal component dispersed therein, and is characterized in that the inorganic oxide comprises titanium oxide and silica and/or zirconia, and the titanium oxide is crystalline titanium oxide.

The titanium oxide is anatase-type titanium oxide, and the crystallite diameter is preferably 100 Å or more.

A content of the metal component in the inorganic oxide particles is preferably in the range from 0.1 to 30% by weight as converted to the metal oxide.

The average particle diameter of the inorganic oxide particles is preferably in the range from 2 to 500 nm, and a concentration of the inorganic oxide particles is preferably in the range from 1 to 20% by weight.

The inorganic oxide particles are preferably colloidal particles of the inorganic oxide.

In a first method of producing an antibacterial deodorant according to the present invention, an aqueous solution of peroxo titanate is obtained by adding hydrogen peroxide to a gel and/or a sol of ortho-titanate; then a dispersion liquid of an inorganic oxide particle precursor is prepared by adding an aqueous solution of a metal component and a silicon compound and/or a zirconium compound into the aqueous solution of peroxo titanate and heating the mixture solution at a temperature of 50° C. or more; further a silicon compound and/or a zirconium compound is added to the mixture solution according to the necessity; and then the resultant mixture solution is subjected to a hydrothermal processing at a temperature in the range from 120 to 280° C. to obtain an antibacterial deodorant, and the deodorant is an inorganic oxide particle dispersion liquid with inorganic oxide particles comprising a metal composition and a an inorganic oxide other than said metal component dispersed therein in which the inorganic oxide contains titanium oxide and/or zirconia, and the titanium oxide is a crystalline titanium oxide.

By drying the inorganic oxide particle dispersion liquid to obtain powder of inorganic oxide particles, it is possible to produce an antibacterial deodorant which is inorganic oxide particles comprising a metal component and an inorganic oxide other than the metal component, and also in which the inorganic oxide includes titanium oxide and silica and/or zirconia and the titanium oxide is crystalline titanium oxide.

In a second method of producing an antibacterial deodorant according to the present invention, a dispersion liquid of an inorganic oxide particle precursor is prepared by adding an aqueous solution of a metal component into a colloidal solution with inorganic oxide colloidal particles having negative charge dispersed therein and heating the colloidal solution to 60° C. or more; a silicon compound and/or a zirconium compound is added to the dispersion liquid according to the necessity; and the mixture liquid is subjected to the hydrothermal processing at a temperature in the range from 120 to 280° C. to obtain an antibacterial deodorant, and the antibacterial deodorant is an inorganic oxide particle dispersion liquid with inorganic oxide particles comprising a metal component and an inorganic oxide other than said metal component dispersed therein, in which the inorganic oxide comprises titanium oxide and silica and/or zirconia; and the titanium oxide is crystalline titanium oxide.

By drying the inorganic oxide particle dispersion liquid to obtain powder of inorganic oxide particles, it is possible to produce an antibacterial deodorant which is inorganic oxide particles comprising a metal component and an inorganic oxide other than the metal component, and also in which the inorganic oxide includes titanium oxide and silica and/or zirconia and the titanium oxide is crystalline titanium oxide.

In a third method of producing a antibacterial deodorant according to the present invention, an antibacterial deodorant is produced through the following steps:

(1) preparing a hydrated oxide by adding an alkali into an aqueous solution obtained by mixing an aqueous solution containing an antibacterial metal component with an aqueous solution of titanate;

(2) washing the obtained hydrated oxide;

(3) suspending the washed hydrated oxide in water;

(4) adding a silica colloidal solution and/or a silicic acid solution in the suspension and agitating the mixture solution;

(5) further adding an alkali into the suspension to adjust in a range from pH 7 to pH 13; and (6) subjecting the pH-adjusted suspension to a hydrothermal processing at a temperature in a range from 110 to 250°

C. to obtain a colloidal solution with crystalline titanium oxide particles dispersed therein.

By drying the colloidal solution obtained in the step (6) above to obtain powder of inorganic oxide particles, it is possible to produce an antibacterial deodorant which is inorganic oxide particles comprising a metal component and an inorganic oxide other than the metal component, and also in which the inorganic oxide includes crystalline titanium oxide and silica.

The antibacterial deodorant according to the present invention has, in addition to the antibacterial activity, excellent photocatalytic activity and high odor-eliminating effect.

With the method according to the present invention, an antibacterial deodorant with excellent stability can be obtained through simple operations.

DETAILED DESCRIPTION OF PREFERRED EMBODIMENTS

[Antibacterial Deodorant]
First Antibacterial Deodorant

A first antibacterial deodorant according to the present invention is inorganic oxide particles comprising a metal component and an inorganic oxide other than the metal component, and the inorganic oxide comprises titanium oxide and silica and/or zirconia, and the titanium oxide is crystalline titanium oxide.

Inorganic Oxide Particles

The inorganic oxide particle according to the present invention comprises a metal component and an inorganic oxide other than the metal component.

Metal Component

In the present invention, the metal component has the antibacterial activity as well as the odor-eliminating activity, and the metal component form particles in a form of a mixture or a compound with an inorganic oxide described later, or is bonded to a surface of the inorganic oxide particle.

The metal component includes, but not limited to, silver, copper, zinc, tin, lead, bismuth, cadmium, chromium, and mercury. Especially, a metal component selected from a group consisting of silver, copper, and zinc is preferable from the view points for the antibacterial activity, odor-eliminating activity, discoloring, safety to the human body, and the like.

A copper ion as an antibacterial component as well as a odor-eliminating component has a blue color, but a silver ion itself is colorless. However, the silver ions are changed into agglomerate of metal silver or an oxide with the color turned into brown or black due to the photochemical reaction or oxidation. Especially, to prevent the silver component from being discolored due to the photochemical reaction caused by ultraviolet rays, it is desirable to use the silver component in combination with titanium, zirconium, or the like. The reason is that such a material as titanium, zirconium, or the like acts as an ultraviolet absorbent to prevent the silver component from being discolored.

A quantity of the metal component in the first antibacterial deodorant (inorganic oxide particles) according to the present invention is preferably in the range from 0.1 to 30% by weight based on the solid phase as converted to an oxide thereof, and more preferably in the range from 0.1 to 15% by weight. When the content of the metal component is less than 0.1% by weight, sometimes the antibacterial activity and odor-eliminating activity may not sufficiently be shown. On the contrary, when the content of the metal component is more than 30% by weight, the antibacterial activity and odor-eliminating activity of the antibacterial deodorant are not substantially different from that when the content is 30% by weight, and when a content of the silver component is too large, sometimes the deodorant may be discolored.

Inorganic Oxide

In the present invention, the inorganic oxide other than the metal component comprises titanium oxide and silica and/or zirconia.

Because the titanium oxide is included therein, the inorganic oxide is activated by the external energy such as light or heat with the odor-eliminating activity and photocatalytic activity improved, so that an antibacterial deodorant with excellent antibacterial activity can be obtained.

A content of the titanium oxide in the inorganic oxide particles is preferably in the range from 50 to 95% by weight, and more preferably in the range from 70 to 90% by weight. When the content of titanium oxide in the inorganic oxide particles is less than 50% by weight, sometimes the sufficient odor-eliminating activity and photocatalytic activity may not be obtained. When the content of titanium oxide in the inorganic oxide particles is over 95% by weight, the content of silica and/or zirconia described hereinafter is too small with the stability degraded, and sometimes the inorganic oxide particles in the inorganic oxide particles dispersion liquid or in the coating liquid for forming a coating film may coagulate, which may lead to degradation of the transparency of the obtained coating film or separation of the coating film.

When silica is contained therein, the stability is improved, and the inorganic oxide particles in the inorganic oxide particles dispersion liquid or in the coating liquid for forming a coating film are more homogeneously dispersed, and the obtained coating film has the excellent adhesiveness to a base material and excellent transparency.

A content of silica in the inorganic oxide particles is preferably in the range from 0 to 30% by weight, and more preferably in the range from 1 to 20% by weight. When the inorganic oxide particles do not contain silica therein, the stability is insufficient although the stability also depends on a content of zirconia, and sometimes the obtained coating film may have low transparency or peel off from the base material as described above. Even when the content of silica in the inorganic oxide particles is over 30% by weight, the stability is not further improved, and sometimes lowering of a content of titanium oxide may lead to lowering of the odor-eliminating activity.

Further because zirconia is contained therein, the stability is improved with the resistance of the obtained antibacterial deodorant against light and weather conditions also improved, and discoloring can be suppressed when a preferable type of metal component such as silver is contained therein.

A content of zirconia in the inorganic oxide particles is preferably in the range from 0 to 30% by weight, and further in the range from 1 to 20% by weight. When the inorganic oxide particles do not contain zirconia, the stability is insufficient although it depends on the content of silica, and sometimes the resistance of the obtained antibacterial deodorant against light and weather conditions as described above may not be obtained, and further discoloring may not be suppressed according to a type of metal component used therein. Even when the content of zirconia in the inorganic oxide particles is over 30% by weight, the stability is not further improved, nor is further improved the resistance of the obtained antibacterial deodorant against light and weather conditions.

The titanium oxide is crystalline titanium oxide, and is preferably anatase-type titanium oxide. As the crystalline titanium oxide, there are anatase-type titanium oxide, rutile-type titanium oxide, and brookite-type titanium oxide. When the crystalline titanium oxide as described above is contained therein, the photoactive characteristics is improved and the excellent odor-eliminating activity is provided. Especially, the anatase-type titanium oxide can be obtained through the hydrothermal processing at a relatively low temperature, and provides an antibacterial deodorant with excellent odor-eliminating performance.

A crystalline diameter of the anatase-type titanium oxide is preferably 100 Å or more. When the crystalline diameter is smaller than 100 Å, sometimes the photocatalytic activity provided by the titanium oxide may be weak. The crystalline diameter of the anatase-type titanium oxide is further preferably in the range from 110 to 350 Å. The crystalline diameter of the titanium oxide can be obtained through the Debye-Sherrer expression from a half width of a face-to-face clearance d=3.52 Å (2θ=25.3 degrees) (CuKα) of a (101) face obtained by X-ray diffraction.

The inorganic oxide according to the present invention may further contain, in addition to titanium oxide, silica, and zirconia, such materials as $Fe_2O_3$, $Sb_2O_5$, $WO_3$, $SnO_2$, $CeO_2$, MgO and the like according to the necessity. When any of the oxides as described above is contained therein, the odor-eliminating activity for some types of odors may further be improved.

An average diameter of the inorganic oxide particles is preferably in the range from 2 to 500 nm, and more preferably in the range from 3 to 250 nm. As the average diameter of the inorganic oxide particles becomes larger, the transparency of coating films formed with the inorganic oxide particles or products with the inorganic oxide particles mixed therein (antibacterial deodorant) will become worse. To prevent this phenomenon, the average diameter of the inorganic oxide particles is preferably not more than 500 nm.

When the average diameter of the inorganic oxide particles is less than 2 nm, the inorganic oxide particles may easily be agglomerated, which makes it impossible to prepare an antibacterial deodorant having excellent dispersibility and stability, and the obtained antibacterial deodorant may not show the sufficient performance.

Second Antibacterial Deodorant

A second antibacterial deodorant according to the present invention is a dispersion liquid of inorganic oxide particles with inorganic oxide particles comprising a metal component and an inorganic oxide other than the metal component dispersed therein, and is characterized in that the inorganic oxide contains titanium oxide and silica and/or zirconia, and that the titanium oxide is crystalline titanium oxide.

The inorganic oxide particles in the first antibacterial deodorant may be used as inorganic oxide particles in the second antibacterial deodorant.

A concentration of the inorganic oxide particles in the inorganic oxide particles dispersion liquid varies according to applications, and there is no specific restriction over the concentration, and the concentration is preferably in the range from 1 to 20% by weight, and more preferably in the range from 1 to 10% by weight as converted to a weight of oxide thereof. When the concentration of the inorganic oxide particles is less than 1% by weigh as converted to the oxide, the concentration is too low and a range of applications thereof is limited, while, when the concentration of the inorganic oxide particles is over 20% by weight as converted to the oxide thereof, the stability may be insufficient in a case where a content of silica and/or zirconia is low.

The inorganic oxide particles in the inorganic oxide particles dispersion liquid is preferably colloidal particles of the inorganic oxide. Namely the dispersion liquid is preferably in the colloidal solution in which the inorganic oxide particles are electrified with the same polarity and repel to each other. When the inorganic oxide particles are colloidal particles of inorganic oxide, an antibacterial deodorant with excellent transparency can be obtained, and the antibacterial deodorant can be advantageously used in applications each requiring the transparency.

[Method of Producing the Antibacterial Deodorant]

Then, a preferably method of producing the antibacterial deodorant described above is described below.

The inorganic oxide particles and inorganic oxide particles dispersion liquid each as the antibacterial deodorant according to the present invention can be produced according to a method of producing a complex oxide colloidal solution described, for instance, in Japanese patent No. HEI 5-132309. Namely, inorganic oxide colloidal particles containing an antibacterial metal component are generated by adding a silicate of an alkali metal, ammonium or an organic base, an alkali-soluble inorganic oxide, and an aqueous solution of an antibacterial metal component at the same time to an alkali aqueous solution with pH of 10 or more.

First Method of Producing an Antibacterial Deodorant

In a preferable method of producing the antibacterial deodorant according to the present invention, at first, a dispersion liquid of complex particles (inorganic oxide particles precursor) including amorphous titanium oxide is prepared according to the method described in Japanese Patent Laid-Open Publication No. SHO 63-270620. Then the dispersion liquid is subjected to a hydrothermal processing at a high temperature to obtain an inorganic oxide particles dispersion liquid containing crystalline titanium oxide.

More specifically, a titanium compound is hydrolyzed according to the known method to prepare a sol or a gel of orthotitanic acid. A gel of orthotitanic acid can be obtained, for instance, by using a titanate such as titanium chloride, titanium sulfate and titanyl sulfate, adding an alkali to an aqueous solution of the titanium compound for neutralizing the aqueous solution, and washing the solution. A sol of orthotitanic acid can be obtained by passing an aqueous solution of a titanium salt through ion-exchange resin to remove anions, or by adding an acid or an alkali in titanium alkoxide such as titanium tetramethoxide, titanium tetraethoxide, titanium tetraisopropoxide, dissolved in water and/or an organic solvent and hydrolyzing the mixture.

pH of the titanium compound solution in the neutralizing or hydrolyzing step is preferably in the range from 6 to 13. When pH of the titanium compound solution is within the range described above, a gel or a sol of orthotitanic acid having high specific surface area can be obtained.

Orthotitanic acid particles in the gel or sol obtained in this step is preferably amorphous.

Next, a peroxotitanic acid aqueous solution is prepared by adding hydrogen peroxide in a gel or a sol of orthotitanic acid or in a mixture thereof to dissolve the gel or sol of orthotitanic acid.

When an aqueous solution of peroxotitanic acid is prepared, a gel or a sol of orthotitanic acid of orthotitanic acid or a mixture thereof is heated to and agitated at a temperature higher than about 50° C. according to the necessity, or to preferably a temperature in the range from 60 to 100° C. Further, if the concentration of the orthotitanic acid is too high, a long period of time is required for dissolving the orthotitanic acid, and sometimes the sol not dissolved yet may be precipitated or the obtained peroxotitanic acid aqueous solution may have a viscosity. To prevent this phenomenon, a concentration of $TiO_2$ is preferably not more than about 10% by weight, and more preferably not more than about 5% by weight.

When a quantity of hydrogen peroxide to be added is 1 or more as expressed with a weight ratio of $H_2O_2/TiO_2$ (orthotitanic acid converted to $TiO_2$), the orthotitanic acid can be completely dissolved. When the weight ratio of $H_2O_2/TiO_2$ is less than 1, the orthotitanic acid is not completely dissolved, and the gel or sol not reacted yet may remain. As the weight ratio of $H_2O_2/TiO_2$ is larger, a dissolving speed of orthotitanic acid is higher and the reaction time is shorter, but even if an excessive quantity of hydrogen peroxide is used, hydrogen peroxide not reacted remains in the reaction system, which is not economical. When the quantity of hydrogen peroxide as described above is used, orthotitanic acid is dissolved within a period of time in the range from 0.5 to 20 hours.

An aqueous solution of a metal component and an aqueous solution or a dispersion liquid of a silicon compound and/or a zirconium compound is added to an aqueous solution of peroxotitanic acid, and the mixture solution is heated to a temperature in the range from 50 to 100° C. to prepare a dispersion liquid of inorganic oxide particles precursor.

A concentration of the peroxotitanic acid is preferably in the range from 0.1 to 5% by weight as converted titanium oxide, and further preferably in the range from 0.2 to 3% by weight. When the concentration of the titanic acid aqueous solution is less than 0.1% by weight as converted to titanium oxide, the yield is low, and the production efficiency drops. When the concentration of the titanic acid aqueous solution is over 5% by weight, diameters of obtained particles of inorganic oxide particles precursor may be unhomogeneous and the precursor particles may be agglomerated, and therefore not only the transparency and adhesiveness, but also the antibacterial activity and odor-eliminating activity of the antibacterial deodorant finally obtained may be insufficient.

As the aqueous solution of the metal component, there can be enlisted aqueous solutions of nitrates, sulfates, chlorides and complex salts of silver, copper, zinc, tin, lead, bismuth, cadmium, chromium, mercury, and the like. Of these materials, an aqueous solution of an ammine complex salt of such materials as zinc, silver, and copper obtained by dissolving zinc oxide, silver oxide, and copper oxide, and the like in ammonium water may advantageously be used.

As for the amount of used metal component, a content of a metal component in the inorganic oxide particles finally obtained is preferably in the range from 0.1 to 30% by weight as converted to an oxide thereof, and more preferably in the range from 0.1 to 15% by weight.

There is not specific restriction over the silicon compound to be used on the condition that the silicon compound can form a complex with titanium oxide to improve the dispersibility and dispersion inorganic oxide particles stability and the titanium oxide constituting the finally obtained inorganic oxide particles is crystalline titanium oxide, and any of known silicon compounds may be used. For instance, any of organic silicon compounds such as tetraalkoxy silane, alkali silicate, an acidic silicic acid solution obtained by dealkylating the alkali silicate, silica sol, and the like may be used for this purpose. Especially the silica sol is preferable because the dispersibility and dispersion stability of the inorganic oxide particles finally obtained are high, which makes it possible to obtain the inorganic oxide particles including crystalline titanium oxide having the high crystallinity.

As for an amount of used silicon compound, a content of silicon in the inorganic oxide particles finally obtained is preferably in the range from 1 to 30% by weight as converted to an oxide thereof (silica), and more preferably in the range from 2 to 20% by weight.

As for the zirconium compound, there is no specific restriction so far as the zirconium compound can form a complex with titanium oxide and also can improve, in addition to dispersibility and dispersion stability, the resistance against light and weather conditions, and also so far as the titanium oxide constituting the inorganic oxide particles finally obtained is crystalline titanium oxide, and any known zirconium compound may be used. For instance, organic zirconium compounds such as tetraalkoxy zirconium, zirconium salts such as zirconium chloride, and zirconia sol may be used for this purpose. Especially zirconia sol is preferable because the resistance of the inorganic oxide particles finally obtained against climate conditions is high and inorganic oxide particles containing crystalline titanium oxide with high crystallinity can be obtained.

As for an amount of used zirconium compound, a content of zirconium in the inorganic oxide particles finally obtained is preferably in the range from 1 to 30% by weight and further preferably in the range from 2 to 20% by weight as converted to an oxide thereof (zirconia).

When the temperature employed for heating is less than 50° C., the stability and dispersion stability of the obtained inorganic oxide particles precursor is insufficient, and the inorganic oxide particles precursor be easily agglomerated, and when the temperature for heating is over 100° C., the antibacterial activity and odor-eliminating activity of the finally obtained inorganic oxide particles may be insufficient due to an amount of used metal component.

A silicon compound and/or a zirconium compound is again added to the dispersion liquid of inorganic oxide particles precursor, and the mixture solution is subjected to the hydrothermal processing at a temperature in the range from 120 to 280° C. and more preferably in the range from 140 to 250° C. A concentration of the dispersion liquid of inorganic oxide particles precursor is preferably in the range from 0.1 to 20% by weight, and more preferably in the range from 0.5 to 10% by weight as converted to an oxide thereof.

As the silicon compound and/or the zirconium compound, any of those described above may be used, and especially the silica sol and zirconia sol may advantageously be used. When the silicon compound and/or zirconium compound is used, even if the compound is subjected to the hydrothermal processing at a high temperature to form particles including crystalline titanium oxide, the inorganic oxide particles are not agglomerated, and an antibacterial deodorant comprising monodispersed inorganic oxide particles can be obtained.

As for an amount of the silicon compound and/or zirconium compound used in this step, like in the case described above, a content of silicon and/or zirconium in the finally obtained inorganic oxide particles is preferably in the range from 1 to 30% by weight and more preferably in the range from 2 to 20% by weight as converted to an oxide thereof.

When the temperature employed for hydrothermal processing is lower than 120° C., titanium oxide in the inorganic oxide particles is not crystallized, and the odor-eliminating performance associated with the odor-eliminating activity and photocatalytic activity is insufficient. When the temperature employed for the hydrothermal processing is over 280° C., the antibacterial activity and odor-eliminating activity may be insufficient for some content of the metal component.

A period of time required for the hydrothermal processing varies according to the temperature employed, and there is not specific restriction over the period so far as crystalline titanium oxide is present in the obtained inorganic oxide particles, but the period is generally in the range from 1 to 48 hours.

[Second Method of Producing the Antibacterial Deodorant]

As a second preferable method, there is the method in which, after an aqueous solution of a metal component is added to a colloidal solution with inorganic oxide colloidal particles having negative charge dispersed therein according to the procedure in the method of producing an antibacterial agent comprising a colloidal solution of the antibacterial inorganic oxide disclosed in Japanese Patent Laid-Open Publication No. HEI 6-80527 (Patent document 6), the colloidal solution is subjected to heating at a temperature of 60° C. and preferably at a temperature in the range from 100 to 200° C. to prepare a dispersion liquid of inorganic oxide particles precursor; then, a silicon compound and/or a zirconium compound is added therein according to the necessity; and finally the mixture solution is subjected to hydrothermal processing at a temperature, like in the first method, in the range from 120 to 280° C., and more preferably at a temperature in the range from 140 to 250° C.

As the aqueous solution of the metal component, like in the first method, aqueous solutions of nitrate, sulfate, chloride, complex salts and the like of silver, copper, zinc, tin, lead, bismuth, cadmium, chromium, mercury and the like may be used. Among these materials, an aqueous solution of ammine complex salt of zinc, silver, copper and the like, which can be obtained by dissolving zinc oxide, silver oxide, and copper oxide in ammonia water may advantageously be used.

As for an amount of used metal component, a content of the metal component in the finally obtained inorganic oxide particles is preferably in the range from 0.1 to 30% by weight, and more preferably in the range from 0.1 to 15% by weight.

A type and an amount of the silicon compound and/or zirconium compounds are as described above.

Water as a dispersion medium for the dispersion liquid of inorganic oxide particles obtained by the production method above may be replaced with an organic solvent by any known method such as the ultrafilter membrane to obtain an antibacterial deodorant comprising a colloidal solution of the antibacterial inorganic oxide containing the organic solvent as a dispersion medium. The organic solvent available for this purpose includes, but not limited to alcohols such as methyl alcohol ethyl alcohol, isopropyl alcohol; cellosolves such as methyl cellosolve, ethyl cellosolve; glycols such as ethylene glycol; esters such as methyl acetate, ethyl acetate; ketones such as acetone, methylethyl ketone; ethers such as diethyl ether, tetrahydrofuran; aromatic carbon hydride such as toluene, xylene; carboxylic acids; and N,N-dimethyl formamide. These organic solvents may be used as a combination of the two or more.

A concentration of the dispersion liquid of inorganic oxide particles can be adjusted to a desired level by any known method such as the ultrafilter membrane.

A second antibacterial deodorant (dispersion liquid of inorganic oxide particles) according to the present invention can be obtained as described above. Further, by drying the obtained dispersion liquid of inorganic oxide particles according to the necessity, the first antibacterial deodorant (inorganic oxide particles powder) according to the present invention can be obtained.

Third Method of Producing the Antibacterial Deodorant

A third method of producing the antibacterial deodorant according to the present invention comprises the steps of: (1) preparing a hydrated oxide by adding an alkali into an aqueous solution obtained by mixing an aqueous solution containing an antibacterial metal component with an aqueous solution of titanate; (2) washing the obtained hydrated oxide; (3) suspending the washed hydrated oxide in water; (4) adding a silica colloidal solution and/or a silicic acid solution in the suspension and agitating the mixture solution; (5) further adding an alkali into the suspension to adjust pH in a range from 7 to 13; and (6) subjecting the pH-adjusted suspension to a hydrothermal processing at a temperature in a range from 110 to 250° C. to obtain a colloidal solution with crystalline titanium oxide particles dispersed therein.

The third method of producing the antibacterial deodorant according to the present invention is described in detail according to the order of steps.

Step (1)

Generally, a metal component having the antibacterial activity and/or odor-eliminating activity may be used as an antibacterial metal component for the present invention, and more specifically any metal component such as silver, copper, zinc, cadmium, mercury, tin, lead, bismuth, iron, cobalt, nickel, rhodium, palladium, platinum, manganese, chromium, molybdenum, tungsten, vanadium, zirconium may be used in the present invention. Especially it is preferable to use silver, copper, zinc, tin, bismuth, iron, cobalt, nickel, rhodium, palladium, platinum, manganese, molybdenum, tungsten, vanadium and zirconium, because the materials have excellent antibacterial and odor-eliminating activities. It is further preferable to use one or more of antibacterial metal components selected from the group consisting of silver, copper, zinc, platinum, and palladium from the view point of antibacterial and odor-eliminating activities, resistance against discoloring, and safety to human bodies.

As the aqueous solution containing the antibacterial metal component, an aqueous solution of a compound soluble in water or an acidic aqueous solution such as nitrates, sulfates, chlorides of the metal component described above. A concentration of the metal component in the aqueous solution is preferably in the range from 0.1 to 50% by weight as converted to an oxide thereof.

Any aqueous solution of titanium sulfate, titanyl sulfate, titanium chloride and the like may be used as the aqueous solution of titanate. A concentration of the titanate aqueous solution is preferably in the range from 5 to 50% by weight as converted to $TiO_2$.

In step (1), an aqueous solution is prepared by mixing an aqueous solution containing the antibacterial metal component with an aqueous solution of the titanate. A mixing ratio of the aqueous solution containing the antibacterial metal component versus aqueous solution of titanate is preferably in the range from 0.1/100 to 50/100 as expressed with the weight ratio of an oxide of the antibacterial metal component $(MO_x)/TiO_2$. When the weight ratio of $MO_x/TiO_2$ is smaller than 0.1/100, sometimes the antibacterial and odor-eliminating activities become smaller, and when the weight ratio of $MO_x/TiO_2$ is larger than 50/100, the photocatalytic activity may become weaker. The weight ratio of $MO_x/TiO_2$ is more preferably in the range from 1/100 to 20/100.

An alkali such as ammonia water or a sodium hydrate aqueous solution is added to the mixed aqueous solution described above for neutralization with agitation to generate a hydrated oxide of antibacterial metal and titanium. pH of the mixture aqueous solution prepared by mixing the aqueous solution containing the antibacterial metal component with the titanate aqueous solution is preferably adjusted to the range from 6.5 to 7.5.

Step (2)

Byproduct salts are removed by washing the hydrated oxide obtained in step (1) by the ordinary method. By washing the hydrated oxide, it is preferable to reduce a content of byproduct salts in the hydrated oxide to a level of 1% by weight and more preferably to 0.1% by weight on dry basis.

When a content of byproduct salts in the hydrated oxide is more than 1% by weight, sometimes a colloidal solution can not be obtained.

Step (3)

The hydrated oxide obtained in step (2) is suspended in water to obtain a suspension (slurry). A concentration of the suspension is preferably adjusted to the range from 1 to 20% by weight as an oxide thereof.

Step (4)

Next, a silica colloidal solution and/or a silicic acid solution is added and mixed with the suspension. When a silica colloidal solution is used, an average particle diameter of the silica colloidal particles is preferably 30 nm or below, and more preferably 15 nm or below. By adding the silica colloidal solution and/or a silicic acid solution in the suspension, it is possible to obtain a colloidal solution of antibacterial titanium oxide with high concentration and excellent light resistance which is stable for a long period of time.

By controlling a quantity of silica ($SiO_2$) in the silica colloidal solution and/or a silicic acid solution to be added, it is possible to control the diameter of the titanium oxide colloidal particles in the obtained antibacterial titanium oxide colloidal solution. When a quantity of added silica increases, the diameter of the titanium oxide colloidal particles becomes smaller, and on the contrary when the quantity decreases, the diameter of the titanium oxide colloidal particles becomes larger.

A quantity of silica in the silica colloidal solution and/or a silicic acid solution is preferably in the range from 0.5/100 to 30/100, and more preferably in the range from 1/100 to 20/100 as expressed by a weight ratio of $SiO_2/(MOx+TiO_2)$.

Step (5)

Further an alkali is added to the mixed suspension obtained in step (4) to adjust pH of the suspension in the range from 7 to 13. When pH of the suspension is not in the range from 7 to 13, sometimes a colloidal solution with the antibacterial titanium oxide particles dispersed therein may not be generated. pH of the suspension is preferably in the range from 8 to 12, and more preferably in the range from 8 to 10.

Step (6)

The pH-adjusted suspension is subjected to the hydrothermal processing at a temperature in the range from 110 to 250° C. When the temperature is lower than 110° C., sometimes the antibacterial titanium oxide particles may not be generated, and when the temperature is higher than 250° C., the facility cost for the hydrothermal processing becomes higher, which is economically disadvantageous. The hydrothermal processing is continued until a colloidal solution with antibacterial titanium oxide particles dispersed therein is generated, and is generally continued for 1 to 24 hours, and more preferably for 10 to 20 hours in an autoclave at the temperature within the range as described above.

The antibacterial titanium oxide colloidal solution obtained by the method described above is alkaline, but when alkalinity of the antibacterial titanium oxide colloidal solution is not preferable in some applications, the alkali can be removed by washing the antibacterial titanium oxide colloidal solution, for instance, with an ultrafilter membrane device.

EXAMPLES

Example 1

Preparation of the Antibacterial Deodorant (1)

6.25 kg crystal of titanyl sulfate dihydrate (TEIKA K.K.; TM Crystal) was dissolved in 33.75 kg water. Then ammonia water with the concentration of 15% by weight was added for adjusting the pH to about 7 to obtain a gel of orthotitanic acid, which was filtered out and washed with 100 kg water. Washed gel of orthotitanic acid was dispersed in water to obtain a slurry with the total weight of 160 kg. Then the slurry was heated to 50° C., and 12.32 kg hydrogen peroxide with the concentration of 35% by weight was added therein, the mixture solution was agitated for 10 minutes and then heated to 90° C. and heated for two hours to obtain an aqueous solution of peroxotitanic acid with the concentration of 1.2% by weight as $TiO_2$.

Separately, 3648 g water was added to 18.24 g copper nitrate $Cu(NO_3)_2.3H_2O$ to prepare a copper nitrate aqueous solution with the concentration of 0.5% by weight. Then 4.0 kg peroxotitanic acid aqueous solution with the $TiO_2$ concentration of 1% by weight was poured into a beaker and the temperature was adjusted to 50° C. under agitation. The pH was 7.9. The copper nitrate aqueous solution described above was added to the peroxotitanic acid aqueous solution at the rate of 10 g/min. At a point of time when pH of the peroxotitanic acid aqueous solution started dropping in response to addition of the copper nitrate aqueous solution, anion exchange resin (produced by MITSUBISHI KAGAKU K.K.) was added therein little by little to preserve the pH at 7.9, and this operation was continued until addition of all of the copper nitrate aqueous solution was completed. Total consumption of the anion exchange resin was 310 g, and the final pH of the peroxotitanic acid aqueous solution was 8.1. Then, the mixture solution was heated for one hour at 95° C. to prepare a dispersion liquid of inorganic oxide particles precursor.

Then the peroxotitanic acid aqueous solution was washed through an ultrafilter membrane by water with the weight 200 times larger than that of $TiO_2$, and 62.5 g silica sol (produced by Catalysts & Chemicals Ind. Co., Ltd.: SN-350 with the average particle diameter of 10 nm and solid phase concentration of 16% by weight) was added therein, and the mixture solution was subjected to the hydrothermal processing for 16 hours at 155° C. and then condensed to obtain a stable dispersion liquid of copper-carrying inorganic oxide particles (1) with the solid phase concentration of 10% by weight.

The dispersion liquid of copper-carrying inorganic oxide particles (1) was stable even after it was left uncontrolled for one month. A quantity of the metal component carried in the inorganic oxide particles (1) as converted to an oxide thereof, and average diameter of the inorganic oxide particles (1) were measured, and the result is shown in Table 1. The antibacterial performance, odor-eliminating performance, and photocatalytic performance of the dispersion liquid of inorganic oxide particles (1) as an antibacterial deodorant (1) were assessed, and the result is shown in Table 2.

(1) Assessment of the Antibacterial Activity

Testing with *E coli*:

*E. coli* (*Escherichia coli* IFO 3972) was suspended in 50 ml of phosphate buffer liquid with 0.1 g of the antibacterial deodorant (1) added therein, and the liquid was agitated for one hour at the room temperature with the rotation speed of 330 rpm. Then the number of living bacteria (B) was measured.

Separately, the empty test was carried out without adding the antibacterial deodorant (1) but following the same procedure, and the number of living bacteria after addition of *E coli* (A) was measured and the difference (log A–log B) was assessed. The result is shown in Table 2.

The phosphate buffer liquid above is a solution prepared by dissolving 34 g potassium dihydrogenphosphate in 1000 ml water, adjusting pH of the solution with sodium hydroxide to 7.2, and then diluting the pH-adjusted solution with a sodium chloride aqueous solution with the concentration of 0.85% by weight at the dilution ratio of 800 times.

Testing with *Staphylococcus aureuse*:

Assessment was made following the same procedure employed in the testing with *E coli* excluding the point that *staphylococcus* aureuse was used in place of *E coli*, and the result is shown in Table 2.

(2) Assessment of the Odor-Eliminating Performance

The antibacterial deodorant (1) was dried for two hours at 105° C., and then the humidity was adjusted for 24 hours at 20° C. in the relative humidity of 65%. Then 1 g powder of the humidity-adjusted antibacterial deodorant (1) was put in a tetrabag with the capacity of 5 L, and 3 L acetaldehyde odorous gas with the concentration of 14 ppm was filled therein. Then after two hours, the concentration of acetaldehyde was measured with a detection tube (produced by Gastec Corp.: 92 L) to measure a reduction ratio of acetaldehyde as an odor elimination ratio. The result is shown in Table 2.

(3) Assessment of the Photocatalytic Performance

The antibacterial deodorant (1) was dried for two hours at 105° C., and then the humidity was adjusted for 24 hours at 20° C. in the relative humidity of 65%. Then UV ray was irradiated for 24 hours with two black light fluorescent lamps (produced by TOSHIBA Inc.: FL20S-BLB). Then 0.13 g powder of antibacterial deodorant (1) was put in a tetrabag with the capacity of 5 L, and 3 L acetaldehyde odorous gas with the concentration of 100 ppm was filled therein, and the concentration of acetaldehyde was measured with a detection tube (produced by Gastec Corp.: 92 L) to measure a reduction ratio of acetaldehyde as an odor elimination ratio. The result is shown in Table 2.

(4) Weather Resistance

The weather resistance testing was performed with a weather meter (produced by Gas Tester Corp.) by irradiating UV ray for 100 hours to powder of the antibacterial deodorant (1), and a degree of discoloring was observed.

○: Discoloring not observed
Δ: Discoloring slightly observed
x: Discoloring observed (5) Discoloring A 10 cm×10 cm gauze was immersed in the antibacterial deodorant (1) with the concentration adjusted to 1% by weight, and then was dried under the solar light. During the drying process, a degree of discoloring to brown or black was observed, as free Ag ions were reduced to Ag due to the UV ray.

○: Discoloring not observed
Δ: Discoloring slightly observed
x: Discoloring observed Example 2

Preparation of the Antibacterial Deodorant (2)

A dispersion liquid of copper-carrying inorganic oxide particles (2) with the solid phase concentration of 10% by weight was obtained according to the procedure employed in Example 1 excluding the point that the hydrothermal processing was carried out at 200° C.

The dispersion liquid of copper-carrying inorganic oxide particles (2) was stable even after the dispersion liquid was left uncontrolled for one month. A quantity of the metal component carried in the inorganic oxide particles (2) as converted to an oxide thereof, and average diameter of the inorganic oxide particles (2) were measured, and a result is shown in Table 1. The antibacterial performance, odor-eliminating performance, and photocatalytic performance of the dispersion liquid of inorganic oxide particles (2) as an antibacterial deodorant (2) were assessed, and a result is shown in Table 2.

Example 3

A dispersion liquid of zinc-carrying inorganic oxide particles (3) with the solid phase concentration of 10% by weight was obtained according to the procedure employed in Example 1 excluding the point that 14.6 g zinc nitrate $Zn(NO_3)_2.6H_2O$ was used in place of copper nitrate $Cu(NO_3)_2.3H_2O$.

The dispersion liquid of zinc-carrying inorganic oxide particles (3) was stable even after the dispersion liquid was left uncontrolled for one month. A quantity of the metal component carried in the inorganic oxide particles (3) as converted to an oxide thereof, and average diameter of the inorganic oxide particles (3) were measured, and a result is shown in Table 1. The antibacterial performance, odor-eliminating performance, and photocatalytic performance of the dispersion liquid of inorganic oxide particles (3) as an antibacterial deodorant (3) were assessed, and a result is shown in Table 2.

Example 4

Preparation of the Antibacterial Deodorant (4)

A dispersion liquid of silver-carrying inorganic oxide particles (4) with the solid phase concentration of 10% by weight was obtained according to the procedure employed in Example 1 excluding the point that 3.68 g silver nitrate $AgNO_3$ was used in place of copper nitrate $Cu(NO_3)_2.3H_2O$.

The dispersion liquid of silver-carrying inorganic oxide particles (4) was stable even after the dispersion liquid was left uncontrolled for one month. A quantity of the metal component carried in the inorganic oxide particles (4) as converted to an oxide thereof, and average diameter of the inorganic oxide particles (4) were measured, and a result is shown in Table 1. The antibacterial performance, odor-eliminating performance, and photocatalytic performance of the dispersion liquid of inorganic oxide particles (4) as an antibacterial deodorant (4) were assessed, and a result is shown in Table 2.

Example 5

Preparation of the Antibacterial Deodorant (5)

A dispersion liquid of silver-carrying inorganic oxide particles (5) with the solid phase concentration of 10% by weight was obtained according to the procedure employed in Example 4 excluding the point that 31.3 g of silica sol (produced by Catalysts & Chemicals Ind. Co., Ltd.: SN-350, average particle diameter: 10 nm, solid phase concentration: 16% by weight) was used.

The dispersion liquid of silver-carrying inorganic oxide particles (5) was stable even after the dispersion liquid was left uncontrolled for one month. A quantity of the metal component carried in the inorganic oxide particles (5) as converted to an oxide thereof, and average diameter of the inorganic oxide particles (5) were measured, and a result is shown in Table 1. The antibacterial performance, odor-eliminating performance, and photocatalytic performance of the dispersion liquid of inorganic oxide particles (5) as an antibacterial deodorant (5) were assessed, and a result is shown in Table 2.

Example 6

Preparation of the Antibacterial Deodorant (6)

A dispersion liquid of silver-carrying inorganic oxide particles (6) with the solid phase concentration of 10% by weight was obtained according to the procedure employed in Example 4 excluding the point that 31.3 g of silica sol (produced by Catalysts & Chemicals Ind. Co., Ltd.: SN-350, average particle diameter: 10 nm, solid phase concentration: 16% by weight) and 38.5 g of zirconia sol (produced by DAIICHI KIGENSO K. K., AL-7, average particle diameter: 5 nm, solid phase concentration: 13% by weight) were added.

The dispersion liquid of silver-carrying inorganic oxide particles (6) was stable even after the dispersion liquid was left uncontrolled for one month. A quantity of the metal component carried in the inorganic oxide particles (6) as converted to an oxide thereof, and average diameter of the inorganic oxide particles (6) were measured, and a result is shown in Table 1. The antibacterial performance, odor-eliminating performance, and photocatalytic performance of the dispersion liquid of inorganic oxide particles (6) as an antibacterial deodorant (6) were assessed, and a result is shown in Table 2.

Example 7

Preparation of the Antibacterial Deodorant (7)

A dispersion liquid of silver-carrying inorganic oxide particles (7) with the solid phase concentration of 10% by weight was obtained according to the procedure employed in Example 5 excluding the point that 38.5 g of zirconia sol (produced by DAIICHI KIGENSO K.K., AL-7, average particle diameter: 5 nm, solid phase concentration: 13% by weight) was added in place of the silica sol.

The dispersion liquid of silver-carrying inorganic oxide particles (7) was stable even after the dispersion liquid was left uncontrolled for one month. A quantity of the metal component carried in the inorganic oxide particles (7) as converted to an oxide thereof, and average diameter of the inorganic oxide particles (7) were measured, and a result is shown in Table 1. The antibacterial performance, odor-eliminating performance, and photocatalytic performance of the dispersion liquid of inorganic oxide particles (7) as an antibacterial deodorant (7) were assessed, and a result is shown in Table 2.

[Control 1]

Preparation of the Antibacterial Deodorant (R1)

A dispersion liquid of inorganic oxide particle precursor was prepared according to the procedure employed in Example 1.

An aqueous solution of peroxotitanic acid was washed through a ultrafilter membrane by water with the weight 200 times larger than that of $TiO_2$ and then condensed to obtain a dispersion liquid of copper-carrying inorganic oxide particles (R1) with the solid phase concentration of 10% by weight.

After the dispersion liquid of copper-carrying inorganic oxide particles (R1) was left uncontrolled for one month, it was recognized that the transparency lowered and was gelatinated with a portion of the particles settled down. A quantity of the metal component carried in the inorganic oxide particles (R1) as converted to an oxide thereof, and an average diameter of the inorganic oxide particles (R1) were measured, and a result is shown in Table 1. Also the antibacterial performance, odor-eliminating performance, and photocatalytic performance of the dispersion liquid of inorganic oxide particles (R1) as an antibacterial deodorant (R1) were assessed, and a result is shown in Table 2.

[Control 2]

Preparation of the Antibacterial Deodorant (R2)

A dispersion liquid of a zinc-carrying inorganic oxide particles (R2) with the solid phase concentration of 10% by weight was obtained according to the procedure employed in Control 1 excluding the point that 14.6 g zinc nitrate $Zn(NO_3)_2.6H_2O$ was used in place of copper nitrate $Cu(NO_3)_2.3H_2O$.

After the dispersion liquid of zinc-carrying inorganic oxide particles (R2) was left uncontrolled for one month, it was recognized that the transparency lowered and was gelatinated with a portion of the particles settled down. A quantity of the metal component carried in the inorganic oxide particles (R2) as converted to an oxide thereof, and an average diameter of the inorganic oxide particles (R2) were measured, and a result is shown in Table 1. Also the antibacterial performance, odor-eliminating performance, and photocatalytic performance of the dispersion liquid of inorganic oxide particles (R2) as an antibacterial deodorant (R2) were assessed, and a result is shown in Table 2.

[Control 3]

Preparation of the Antibacterial Deodorant (R3)

A dispersion liquid of a silver-carrying inorganic oxide particles (R3) with the solid phase concentration of 10% by weight was obtained according to the procedure employed in Control 1 excluding the point 14.6 g silver nitrate $AgNO_3$ was used in place of copper nitrate $Cu(NO_3)_2.3H_2O$.

After the dispersion liquid of silver-carrying inorganic oxide particles (R3) was left uncontrolled for one month, it was recognized that the transparency lowered and was gelatinated with a portion of the particles settled down. A quantity of the metal component carried in the inorganic oxide particles (R3) as converted to an oxide thereof, and an average diameter of the inorganic oxide particles (R3) were measured, and a result is shown in Table 1. Also the antibacterial performance, odor-eliminating performance, and photocatalytic performance of the dispersion liquid of inorganic oxide particles (R3) as an antibacterial deodorant (R3) were assessed, and a result is shown in Table 2.

[Control 4]

Preparation of the Antibacterial Deodorant (R4)

A dispersion liquid of inorganic oxide particle precursor was prepared according to the procedure employed in Example 5 and then condensed to obtain a dispersion liquid of the silver-carrying inorganic oxide particles (R4) with the solid phase contents of 10% by weight.

After the dispersion liquid of silver-carrying inorganic oxide particles (R4) was left uncontrolled for one month, it was recognized that a portion of the particles settled down. A quantity of the metal component carried in the inorganic oxide particles (R4) as converted to an oxide thereof, and an average diameter of the inorganic oxide particles (R4) were measured, and a result is shown in Table 1. Also the antibacterial performance, odor-eliminating performance, and photocatalytic performance of the dispersion liquid of inorganic oxide particles (R4) as an antibacterial deodorant (R4) were assessed, and a result is shown in Table 2.

[Control 5]

Preparation of the Antibacterial Deodorant (R5)

A dispersion liquid of inorganic oxide particle precursor was prepared according to the procedure employed in Example 7 and then condensed to obtain a dispersion liquid of the silver-carrying inorganic oxide particles (R5) with the solid phase contents of 10% by weight.

After the dispersion liquid of silver-carrying inorganic oxide particles (R5) was left uncontrolled for one month, it was recognized that a portion of the particles settled down. A quantity of the metal component carried in the inorganic oxide particles (R5) as converted to an oxide thereof, and an average diameter of the inorganic oxide particles (R5) were measured, and a result is shown in Table 1. Also the antibacterial performance, odor-eliminating performance, and photocatalytic performance of the dispersion liquid of inorganic oxide particles (R5) as an antibacterial deodorant (R5) were assessed, and a result is shown in Table 2.

The hydrated oxide was filtered with a flat filter, washed by sprinkling 100 kg deionized water thereon to obtain hydrated oxide with by-product material removed therefrom. A quantity of $SO_4$ in the hydrated oxide was 0.1% by weight (as converted to dry weight).

Next, the washed hydrated oxide was diluted with water to prepare 20.1 kg of a suspension with the solid content concentration of 5% by weight. To the suspension was added 940

TABLE 1

| | Dispersion liquid of inorganic oxide particles | | | | | | | | |
|---|---|---|---|---|---|---|---|---|---|
| | Inorganic oxide | | | Metal component | | Hydrothermal process. temp. | Crystallinity of titanium | Av. particle diameter | Conc. |
| | $TiO_2$ wt % | $SiO_2$ wt % | $ZrO_2$ wt % | Type | Content* wt % | °C. | oxide | nm | wt % |
| Example 1 | 66.5 | 20.0 | — | Cu | 13.5 | 155 | anatase | 12.3 | 10 |
| Example 2 | 66.5 | 20.0 | — | Cu | 13.5 | 200 | anatase | 13.6 | 10 |
| Example 3 | 71.9 | 19.8 | — | Zn | 8.3 | 155 | anatase | 11.3 | 10 |
| Example 4 | 76.2 | 18.8 | — | Ag | 5.0 | 155 | anatase | 11.3 | 10 |
| Example 5 | 84.3 | 10.1 | — | Ag | 5.6 | 155 | anatase | 12.1 | 10 |
| Example 6 | 66.2 | 10.1 | 11.2 | Ag | 12.6 | 155 | anatase | 11.5 | 10 |
| Example 7 | 84.3 | — | 10.1 | Ag | 5.6 | 155 | anatase | 12.1 | 10 |
| Control 1 | 85.2 | — | — | Cu | 14.8 | — | amorphous | 10.3 | 10 |
| Control 2 | 90.0 | — | — | Zn | 9.1 | — | amorphous | 10.3 | 10 |
| Control 3 | 94.5 | — | — | Ag | 5.5 | — | amorphous | 10.3 | 10 |
| Control 4 | 84.3 | 10.1 | — | Ag | 5.6 | — | amorphous | 10.3 | 10 |
| Control 5 | 84.3 | — | 10.1 | Ag | 5.6 | — | amorphous | 10.3 | 10 |

*As converted to oxide (CuO, ZnO, $Ag_2O$)

TABLE 2

| | Performance test | | | | | |
|---|---|---|---|---|---|---|
| | Antibacterial performance | | Odor-eliminating performance | Photocatalytic performance | | |
| | E coli difference | staphylococcus aureus difference | Odor-eliminating ratio % | Odor-eliminating ratio % | Light Resist. | Discoloring |
| Example 1 | >5 | >5 | 85 | 100 | ○ | ○ |
| Example 2 | >5 | >5 | 86 | 100 | ○ | ○ |
| Example 3 | >5 | >5 | 80 | 100 | ○ | ○ |
| Example 4 | >5 | >5 | 80 | 100 | ○ | ○ |
| Example 5 | >5 | >5 | 81 | 100 | ○ | ○ |
| Example 6 | >5 | >5 | 81 | 100 | ○ | ○ |
| Example 7 | >5 | >5 | 81 | 100 | ○ | ○ |
| Control 1 | 2.1 | 2.5 | 25 | 65 | X | X |
| Control 2 | 2.0 | 2.0 | 20 | 55 | Δ | Δ |
| Control 3 | 3.0 | 3.5 | 20 | 48 | X | X |
| Control 4 | 2.9 | 3.1 | 20 | 45 | X | X |
| Control 5 | 2.8 | 3 | 20 | 40 | X | X |

Example 8

2.5 kg crystal of titanyl sulfate dihydrate (TEIKA K.K.; TM Crystal) was dissolved by adding 2.5 kg water and was agitated to prepare an aqueous solution of titanyl sulfate. Immediately after that, to 5438 g of the aqueous solution of titanyl sulfate was added 354.6 g zinc sulfate (KANTO KAGAKU K.K. Shika first-class $ZnSO_4.7H_2O$), and was further added 14 kg water to prepare a mixed aqueous solution of titanyl sulfate and zinc sulfate. Then to the mixed aqueous solution was added 15% by weight of ammonia water for adjusting the pH of the mixed aqueous solution to about 7.0 to produce hydrated oxide.

g silica sol (produced by Catalysts & Chemicals Ind. Co., Ltd.: Cataloid-SN350) with the silica concentration of 16% by weight, and further added 3% by weight caustic soda water for adjusting the pH of the suspension to 10.5. Then the pH-adjusted suspension was heated in an autoclave at 160° C. for 16 hours to obtain an antibacterial titanium oxide colloidal solution (A) with zinc-containing titanium oxide colloidal particles dispersed therein.

The antibacterial titanium oxide colloidal solution (A) has the pH of 10.2, solid content concentration of 4.9% by weight, and ZnO content in the solid content of 9.0% by weight. In addition, the average particle diameter (Dp) of zinc-containing titanium oxide colloidal particles in the antibacterial titanium oxide colloidal solution (A) was measured with an ultracentrifugal-type automatic particle size distribution measuring device (measured by HORIBA SEISAKUSHO K.K.: CAPA-700) to find that the average particle diameter was 20.0 nm.

A portion of the antibacterial titanium oxide colloidal solution (A) was dried at 110° C. for 16 hours, and the sample was subjected to X-ray diffraction measurement with an X-ray diffractometer (manufactured by RIGAKU K.K.: RINT-1400), and represented an X-ray diffraction pattern for anatase type titanium oxide with the crystallite diameter thereof being 150 Å. It is to be noted that the antibacterial titanium oxide colloidal solution (A) was in a stable colloidal state even after it was left uncontrolled for one month.

Example 9

An antibacterial titanium oxide colloidal solution (B) with zinc-containing titanium oxide colloidal particles dispersed therein was prepared following the same procedure employed in Example 8 excluding the point that the heat treatment in an autoclave was performed at 120° C. for 16 hours.

The antibacterial titanium oxide colloidal solution (B) has the pH of 10.0, solid content concentration of 4.8% by weight, and ZnO content in the solid content of 9.1% by weight.

In addition, the average particle diameter (Dp) of zinc-containing titanium oxide colloidal particles in the antibacterial titanium oxide colloidal solution (B) was 21.0 nm, and represented an X-ray diffraction pattern for anatase type titanium oxide with the crystallite diameter thereof being 105 Å. It is to be noted that the antibacterial titanium oxide colloidal solution (B) was in a stable colloidal state even after it was left uncontrolled for one month.

Example 10

An antibacterial titanium oxide colloidal solution (C) with copper-containing titanium oxide colloidal particles dispersed therein was prepared following the same procedure employed in Example 8 excluding the point that 312.5 g of copper sulfate (KANTO KAGAKU K.K. Shika first-class, $CuSO_4.5H_2O$) was added in place of zinc sulfate.

The antibacterial titanium oxide colloidal solution (C) has the pH of 10.2, solid content concentration of 5.0% by weight, and CuO content in the solid content of 9.0% by weight.

In addition, the average particle diameter (Dp) of copper-containing titanium oxide colloidal particles in the antibacterial titanium oxide colloidal solution (C) was 22.0 nm, and represented an X-ray diffraction pattern for anatase type titanium oxide with the crystallite diameter thereof being 148 Å. It is to be noted that the antibacterial titanium oxide colloidal solution (C) was in a stable colloidal state even after it was left uncontrolled for one month.

Example 11

An antibacterial titanium oxide colloidal solution (D) with silver-containing titanium oxide colloidal particles dispersed therein was prepared following the same procedure employed in Example 8 excluding the point that 73.5 g of silver nitrate (produced by KANTO KAGAKU K.K. Shika, first-class $AgNO_3$) was added in place of zinc sulfate. The antibacterial titanium oxide colloidal solution (D) has the pH of 10.0, solid content concentration of 4.8% by weight, and $Ag_2O$ content in the solid content of 4.5% by weight.

The antibacterial titanium oxide colloidal solution (D) was washed through an ultrafilter membrane device by deionized water with the weight 200 times larger than the solid content, and was condensed to obtain an antibacterial titanium oxide colloidal solution (D) with silver-containing titanium oxide colloidal particles dispersed therein.

The antibacterial titanium oxide colloidal solution (D) has the pH of 9.3 and solid content concentration of 4.9% by weight.

In addition, the average particle diameter (Dp) of silver-containing titanium oxide colloidal particles in the antibacterial titanium oxide colloidal solution (D) was 18.5 nm, and represented an X-ray diffraction pattern for anatase type titanium oxide with the crystallite diameter thereof being 152 Å. It is to be noted that the antibacterial titanium oxide colloidal solution (D) was in a stable colloidal state even after it was left uncontrolled for one month.

[Control 6]

2.5 kg crystal of titanyl sulfate dihydrate (TEIKA K.K.; TM Crystal) was dissolved by adding 2.5 kg water and was agitated to prepare an aqueous solution of titanyl sulfate. Next, to 2.5 kg of the aqueous solution of titanyl sulfate was further added 5.5 kg water, and then to this aqueous solution is added 15% by weight of ammonia water for adjusting the pH of the aqueous solution to about 7.0 to produce hydrated oxide.

The hydrated oxide was filtered with a flat filter, washed by sprinkling 40 kg deionized water thereon to obtain hydrated oxide with by-product material removed therefrom. A quantity of $SO_4$ in the hydrated oxide was 0.2% by weight (as converted to dry weight).

Next, the washed hydrated oxide was diluted with water to prepare 100 kg of a suspension with the solid content concentration of 1% by weight.

To 40 kg of the suspension was added 2.8 kg hydrogen peroxide with concentration of 35% by weight, and was heated at 90° C. for 2 hours to obtain a titanium oxide colloidal solution with the solid content concentration of 1% by weight.

On the other hand, 3648 g water was added to 12.33 g copper nitrate (KANTO KAGAKU K.K. reagent Shika first-class, $(Cu(NO_3)_2.3H_2O)$) to prepare a copper nitrate aqueous solution with the concentration of 0.5% by weight.

4.0 kg of the titanium oxide colloidal solution was poured into a beaker and the temperature was adjusted to 50° C. under agitation. The pH of the titanium oxide colloidal solution was 7.9 at this point in time. To the titanium oxide colloidal solution was added the copper nitrate aqueous solution described above with a pelister pump at the rate of 10 g/min. At a point of time when pH of the colloidal solution started dropping in response to addition of the copper nitrate aqueous solution, anion exchange resin (produced by MITSUBISHI KAGAKU K. K.) was added therein little by little to preserve the initial pH at 7.9, and this operation was continued until addition of all of the copper nitrate aqueous solution was completed.

Total consumption of the anion exchange resin was 310 g, and the final pH of the colloidal solution was 8.1.

The colloidal solution was washed through an ultrafilter membrane device by deionized water with the weight 200 times larger than that of $TiO_2$, and was condensed to obtain a stable antibacterial titanium oxide colloidal solution (E) with copper-containing titanium oxide colloidal particles dispersed therein with the solid content concentration of 10% by weight. A content of CuO in the solid content of the antibacterial titanium oxide colloidal solution (E) was 9.8% by weight.

In addition, the average particle diameter (Dp) of copper-containing titanium oxide colloidal particles in the antibacterial titanium oxide colloidal solution (E) was 12.0 nm, and represented an X-ray diffraction pattern for amorphism. It is to be noted that the antibacterial titanium oxide colloidal solution (E) was in a stable colloidal state even after it was left uncontrolled for one month.

[Control 7]

A stable antibacterial titanium oxide colloidal solution (F) with zinc-containing titanium oxide colloidal particles dispersed therein with the solid content concentration of 10% by weight was prepared following the same procedure employed in Control 6 excluding the point that 14.6 g of zinc nitrate (KANTO KAGAKU K.K. reagent Shika first-class, (Zn$(NO3)_2 \cdot 6H_2O$) was used in place of copper nitrate. A content of ZnO in the solid content of the antibacterial titanium oxide colloidal solution (F) was 9.1% by weight.

In addition, the average particle diameter (Dp) of zinc-containing titanium oxide colloidal particles in the antibacterial titanium oxide colloidal solution (F) was 15.0 nm, and represented an X-ray diffraction pattern for amorphism. It is to be noted that the antibacterial titanium oxide colloidal solution (F) was in a stable colloidal state even after it was left uncontrolled for one month.

Example 12

A portion of each of the antibacterial titanium oxide colloidal solutions (A) to (D) obtained in Examples 8 to 11 was collected to provide a solution each with the solid content concentration of 3000 ppm. Polyester fiber was immersed into each solution at room temperature for 5 minutes, wrung so that the pickup was 100%, and dried at 80° C. to prepare samples (AF) to (DF) of polyester fiber carrying antibacterial titanium oxide colloidal particles.

[Control 8]

A portion of each of the antibacterial titanium oxide colloidal solutions (E) and (F) obtained in Control 6 and Control 7 was collected to provide a solution each with the solid content concentration of 3000 ppm. Polyester fiber was immersed into each solution at room temperature for 5 minutes, wrung so that the pickup was 100%, and dried at 80° C. to prepare samples (EF) and (FF) of polyester fiber carrying antibacterial titanium oxide colloidal particles.

Assessment Test for Antibacterial Performance 1

A portion of each of the antibacterial titanium oxide colloidal solutions (A) to (D) as well as (E) and (F) obtained in Examples 8 to 11 as well as Control 6 and 7 was dried at 110° C. for 3 hours to prepare samples (AP) to (DP) as well as (EP) and (FP) of each antibacterial titanium oxide powder.

These samples of antibacterial titanium oxide powder were subjected to the following assessment test for antibacterial performance. Namely, $E.\ coli$ ($Escherichia\ coli$ NBRC 3972) and $Staphylococcus\ aureuse$ ($Staphylococcus\ aureuse$ NBRC 12732) were used as test bacteria. The test bacteria were suspended in 50 ml of phosphate buffer liquid, to which 0.1 g of each of the powder samples (AP) to (DP) as well as (EP) and (FP) was added, and the liquid was agitated at room temperature for one hour with the rotation speed of 330 rpm, after which the number of living bacteria was measured. Both the number of living bacteria after 1 hour from the empty test (A) and the number of living bacteria after 1 hour from the antibacterial agent addition testing (B) were measured to make an assessment by the difference (logA–logB). The result of the assessment is shown in Table 3.

TABLE 3

Result of assessment test for antibacterial performance 1

| | Powder sample | Difference | |
| --- | --- | --- | --- |
| | | E coli | Staphylococcus aureuse |
| Example 8 | AP | 3.3 | 4.0 |
| Example 9 | BP | 2.9 | 3.0 |
| Example 10 | CP | >5 | 4.5 |
| Example 11 | DP | >5 | >5 |
| Control 6 | EP | 0.5 | 0.6 |
| Control 7 | FP | 0.9 | 0.8 |

The phosphate buffer liquid above is a solution prepared by dissolving 34 g potassium dihydrogenphosphate in 1000 ml purified water, adjusting pH of the solution with sodium hydroxide to 7.2, and then diluting the pH-adjusted solution with a sodium chloride aqueous solution with the concentration of 0.85% at the dilution ratio of 800 times.

Table 2 demonstrates that the powder sample of titanium oxide whose base is anatase type crystal is more antibacterial than that of amorphous titanium oxide, and, in particular, anatase type titanium oxide having a large crystallite diameter is further more antibacterial.

Assessment Test for Antibacterial Performance 2

Samples (AF) to (DF) as well as (EF) and (FF) of polyester fiber prepared in Example 12 and Control 8 were subjected to an assessment test for antibacterial performance. The assessment test was conducted in accordance with the "Quantitative Antibacterial Performance Testing Method JIS L 1902".

'Test bacteria' $Klebsiella\ pneumoniae$ NBRC13277
$Staphylcoccus\ aureuse$ NBRC12732

'Nutrient': Nutrient broth with the concentration of about 1/20*[1])

(*1) 150 mg/L of meat extract and 250 mg/L of peptone

'Measuring method': 0.4 g of the sample was put in a vial, and 0.2 ml. of a bacterial suspension (with the surfactant Tween80 added thereto with the concentration of 0.05%) was dropped therein. The suspension was cultured at 37° C. for 18 hours, and was washed out to measure the number of living bacteria. The result of the assessment is shown in Table 4.

Table 4 demonstrates that the fiber sample carrying colloidal particles of titanium oxide whose base is anatase type crystal is more antibacterial than that carrying colloidal particles of amorphous titanium oxide.

TABLE 4

Result of assessment test for antibacterial performance 2

| | Fiber sample | Difference | |
| --- | --- | --- | --- |
| | | Klebsiella pneumoniae | Staphylococcus aureuse |
| Example 8 | AF | 4.5 | 4.5 |
| Example 9 | BF | 3.0 | 2.9 |
| Example 10 | CF | 5.0 | >5 |
| Example 11 | DF | >5 | >5 |
| Control 6 | EF | −0.2 | 0.0 |
| Control 7 | FF | −0.3 | 0.3 |

Test for Photocatalytic Effect

Samples of antibacterial titanium oxide powder (AP) to (DP) as well as (EP) and (FP) used in the assessment test for antibacterial performance 1 were employed to conduct an odor-eliminating test by means of light.

2 g of antibacterial titanium oxide powder sample and 1 L of a solution with the acetaldehyde concentration of 400 ppm were put in each pack with the capacity of 1 L, and were illuminated with two black lights (20 W) at 25° C. for 3 hours, after which the concentration of acetaldehyde and $CO_2$ was measured with a detection tube. The result is shown in Table 5.

Table 5 demonstrates that the powder sample of titanium oxide whose base is anatase type crystal has the photocatalytic effect higher than that of amorphous titanium oxide, and, in particular, anatase type titanium oxide with a large crystallite diameter has a further higher photocatalytic effect.

TABLE 5

Result of testing for photocatalytic effect

| | Powder sample | $CO_2$ (ppm) |
|---|---|---|
| Example 8 | AP | 600 |
| Example 9 | BP | 300 |
| Example 10 | CP | 650 |
| Example 11 | DP | 400 |
| Control 6 | EP | 100 |
| Control 7 | FP | 50 |

Assessment Test for Odor-Eliminating Performance 1

Powder samples of antibacterial titanium oxide (AP) to (DP) as well as (EP) and (FP) used in the assessment test for antibacterial performance 1 were employed to conduct an assessment test for odor-eliminating performance.

1 g of antibacterial titanium oxide powder sample, 3 L of ammonia test odorous gas with the initial concentration of 100 ppm, and 3 L of hydrogen sulfide test odorous gas with the initial concentration of 4 ppm were put in each tetrabag with the capacity of 5 L, and were left untouched for 2 hours, after which the concentration of the test odorous gases was measured with a detection tube. The result is shown in Table 6.

Table 6 demonstrates that the powder sample of titanium oxide whose base is anatase type crystal has an odor-eliminating effect higher than that of amorphous titanium oxide, and, in particular, anatase type titanium oxide with a large crystallite diameter has a further higher odor-eliminating effect.

TABLE 6

Result of assessment test for odor-eliminating performance 1

| | Powder sample | Odor-eliminating ratio (%) | |
|---|---|---|---|
| | | Ammonium | Hydrogen sulfide |
| Example 8 | AP | 100 | 100 |
| Example 9 | BP | 98 | 95 |
| Example 10 | CP | 100 | 100 |
| Example 11 | DP | 95 | 85 |
| Control 6 | EP | 70 | 50 |
| Control 7 | FP | 60 | 40 |

Assessment Test for Odor-Eliminating Performance 2

Samples of polyester fiber (AF) to (DF) as well as (EF) and (FF) prepared in Example 12 and Control 8 were employed to conduct an assessment test for odor-eliminating performance.

10×10 cm sample test cloth made of the polyester fiber, 3 L of ammonia test odorous gas with the initial concentration of 100 ppm, and 3 L of hydrogen sulfide test odorous gas with the initial concentration of 4 ppm were put in each tetrabag with the capacity of 5 L, and were left untouched for 2 hours, after which the concentration of the test odorous gases was measured with a detection tube. The result is shown in Table 7.

Table 7 demonstrates that, like Table 6, even when fabricated into fiber, the fiber sample carrying colloidal particles of titanium oxide whose base is anatase type crystal has an odor-eliminating effect higher than that of carrying colloidal particles of amorphous titanium oxide.

TABLE 7

Result of assessment test for odor-eliminating performance 2

| | Fiber sample | Odor-eliminating ratio (%) | |
|---|---|---|---|
| | | Ammonium | Hydrogen sulfide |
| Example 8 | AF | 100 | 100 |
| Example 9 | BF | 85 | 80 |
| Example 10 | CF | 100 | 100 |
| Example 11 | DF | 80 | 70 |
| Control 6 | EF | 60 | 30 |
| Control 7 | FF | 40 | 20 |

What is claimed is:

1. An antibacterial deodorant formed of inorganic particles comprising:
    a metal component having an antibacterial activity and odor-eliminating activity, said metal component being selected from the group consisting of silver, copper and zinc, and
    an inorganic oxide other than said metal component,
    wherein said inorganic oxide comprises crystalline titanium oxide, and at least one of silica and zirconia, which form complex inorganic oxide particles,
    wherein a content of the metal component in the inorganic oxide particles is in a range from 0.1 to 30% by weight as converted to an oxide thereof,
    wherein an average particle diameter of said inorganic oxide particle is in a range from 2 to 500 nm,
    wherein the crystalline titanium oxide is presented in a range of 50-90% by weight,
    wherein the silica is present in a range of 0-30% by weight, and
    wherein the zirconia is present in a range of 0-30% by weight.

2. The antibacterial deodorant according to claim 1, wherein said titanium oxide is anatase-type titanium oxide.

3. The antibacterial deodorant according to claim 2, wherein a crystallite diameter of said anatase-type titanium oxide is 100 Å or more.

4. An antibacterial deodorant formed of a dispersion liquid of inorganic oxide particles comprising;
    a metal component having an antibacterial activity and odor-eliminating activity, said metal component being selected from the group consisting of silver, copper and zinc, and
    an inorganic oxide other than said metal component with the inorganic oxide dispersed in the dispersion liquid,
    wherein said inorganic oxide comprises crystalline titanium oxide, and at least one of silica and zirconia, which form complex inorganic oxide particles,
    wherein a content of said metal component in the inorganic oxide particles is in a range from 0.1 to 30% by weight as converted to an oxide thereof,
    wherein an average particle diameter of said inorganic oxide particles is in a range from 2 to 500 nm and a concentration of the inorganic oxide particles is in a range from 1 to 20% by weight as converted to an oxide thereof, wherein said inorganic oxide particles are colloidal particles of the inorganic oxide, wherein the crystalline titanium oxide is presented in a range of 50-90% by weight, wherein silica is present in a range of 0-30% by weight, and wherein zirconia is present in a range of 0-30% by weight.

5. The antibacterial deodorant according to claim 4, wherein said titanium oxide is anatase-type titanium oxide.

6. The antibacterial deodorant according to claim 5, wherein a crystallite diameter of said anatase-type titanium oxide is 100 Å or more.

7. The antibacterial deodorant according to claim 1, wherein said inorganic oxide comprises said crystalline titanium oxide, silica and zirconia.

8. The antibacterial deodorant according to claim 7, wherein said metal composition comprises copper.

9. The antibacterial deodorant according to claim 4, wherein said inorganic oxide comprises said crystalline titanium oxide, silica and zirconia.

10. The antibacterial deodorant according to claim 9, wherein said metal composition comprises copper.

11. An antibacterial deodorant comprising:

metal particles selected from the group consisting of silver, copper and zinc, and having an antibacterial activity and odor-eliminating activity, and inorganic oxide particles comprising crystalline titanium oxide, and at least one of silica and zirconia, in a form of complex inorganic oxide particles, wherein a content of the metal component in the inorganic oxide particles is in a range from 0.1 to 30% by weight as converted to an oxide thereof, wherein an average particle diameter of said inorganic oxide particle is in a range from 2 to 500 nm, wherein the crystalline titanium oxide is presented in a range of 50-90% by weight, wherein the silica is present in a range of 0-30% by weight, and wherein the zirconia is present in a range of 0-30% by weight.

* * * * *